Figure 1:
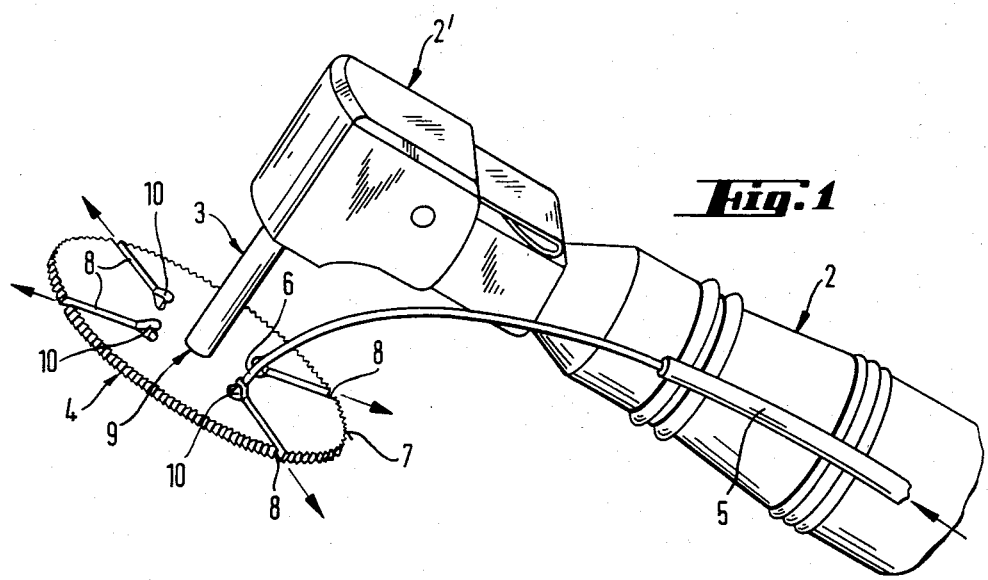

United States Patent [19]

Grafelmann

[11] Patent Number: 4,511,334
[45] Date of Patent: Apr. 16, 1985

[54] DENTAL INSTRUMENT FOR CUTTING SLOTS FOR RECEIVING IMPLANTS INTO THE JAW

[76] Inventor: Hans L. Grafelmann, Parkstrasse 105, 2800 Bremen, Fed. Rep. of Germany

[21] Appl. No.: 523,378

[22] Filed: Aug. 15, 1983

[30] Foreign Application Priority Data

Nov. 25, 1982 [DE] Fed. Rep. of Germany ... 8233133[U]

[51] Int. Cl.³ ............................................. A61C 3/02
[52] U.S. Cl. ...................................... 433/165; 433/82
[58] Field of Search ............................ 76/25; 125/15; 30/123.3; 51/267, 206 R, 170 PT, 170 T; 433/82, 165

[56] References Cited

U.S. PATENT DOCUMENTS 1,117,660  11/1914  Gilmore ................................. 51/267
3,240,243  3/1966   Golick .................................. 51/267
3,663,787  6/1972   Haswell et al. ....................... 51/267

Primary Examiner—Robert Peshock
Attorney, Agent, or Firm—Balogh, Osann, Kramer, Dvorak, Genova & Traub

[57] ABSTRACT

A dental rotary cutting instrument is provided, which is adapted to be driven by a dental handpiece and to cut slots for receiving implants into a jaw. The instrument includes a sawblade, which has a periphery and is provided at the periphery with sawteeth and is formed with a plurality of angularly spaced apart, radial passages, which open at said periphery. Driving and coolant supply means are adapted to be connected to a dental handpiece and to transmit torque from the handpiece to the sawblade to rotate the latter and are adapted to supply a coolant from the handpiece to each of the radial passages at a point which is radially inwardly spaced from the periphery.

12 Claims, 6 Drawing Figures

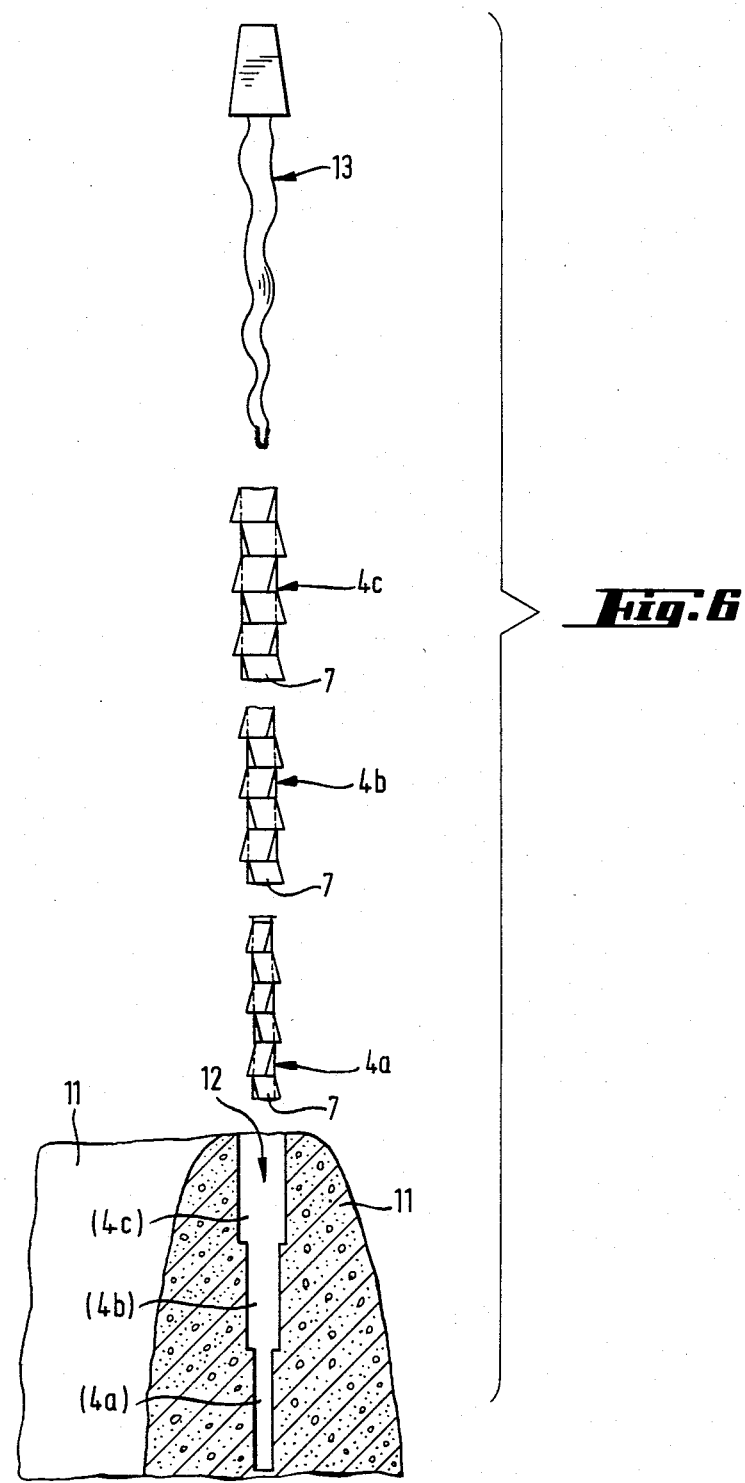

DENTAL INSTRUMENT FOR CUTTING SLOTS FOR RECEIVING IMPLANTS INTO THE JAW

This invention relates to a dental instrument which is adapted to be driven by a dental handpiece and serves to cut slots for receiving implants into a jaw.

It is known that such slots can be cut with a burr, which is caused to drill a hole into the jaw at one point and is then displaced at right angles to the axis of the burr. Because the burr cannot be cooled during this cutting operation in a large depth and is being soiled by the drillings, the burr must often be pulled out, cleaned, and permitted to cool and then be re-inserted. As a result, the slot which has been cut is not defined by straight lines but is formed in its side walls with steps and recesses, which will obstruct the insertion of the implant and may cause the bone to be destroyed.

It is an object of the invention to provide a dental instrument for cutting slots for receiving implants into a jaw while a formation of steps in the resulting slot is avoided.

In accordance with the invention this object is accomplished by the provision of a rotating sawblade having radial slots or bores for conducting a coolant from the central region of the sawblade to the periphery of the sawblade, which is provided with sawteeth at its periphery.

For this purpose the sawblade is suitably formed with a circular series of apertures, which are spaced around the center of the sawblade, and with a plurality of radial slots, which lead from respective ones of the apertures to the periphery of the sawblade, which at its periphery is provided with sawteeth. The coolant is supplied through a hose, which is secured to the handpiece, and emerges from the hose on the inside surface of the sawblade over the circular series of apertures.

Each aperture has preferably a cardioid configuration but may have a different shape too. A slot or groove extends radially outwardly from the apex of the cardioid aperture.

If the sawblade has a sufficiently large thickness, it may be formed with radial or diametrical bores through which the coolant is guided or conducted from the axial bore of the drive shaft to an outlet opening at the periphery of the sawblade.

The sawteeth are preferably set so that they will tend to retain the coolant, which is caused to flow off radially by centrifugal force. This purpose is also served by the apertures. As a result, coolant is supplied at a relatively high rate to the working or cutting region in the depth.

The cut which is formed by the circular saw has rounded corners. By means of a burr, the corners may be milled to be right-angled if this is necessary in view of the shape of the implant to be inserted.

If the implant is wedge-shaped or corrugated in cross-section the slot which is cut into the jaw is suitably also wedge-shaped in cross-section. This is accomplished in accordance with the invention by means of sawblades which have graded thicknesses and which are used in such a manner that the thickest sawblade is used to cut to the smallest depth and the thinnest sawblade is used to cut to the largest depth.

The drawing shows two preferred embodiments of the invention in diagrammatic perspective views.

Figure 2:
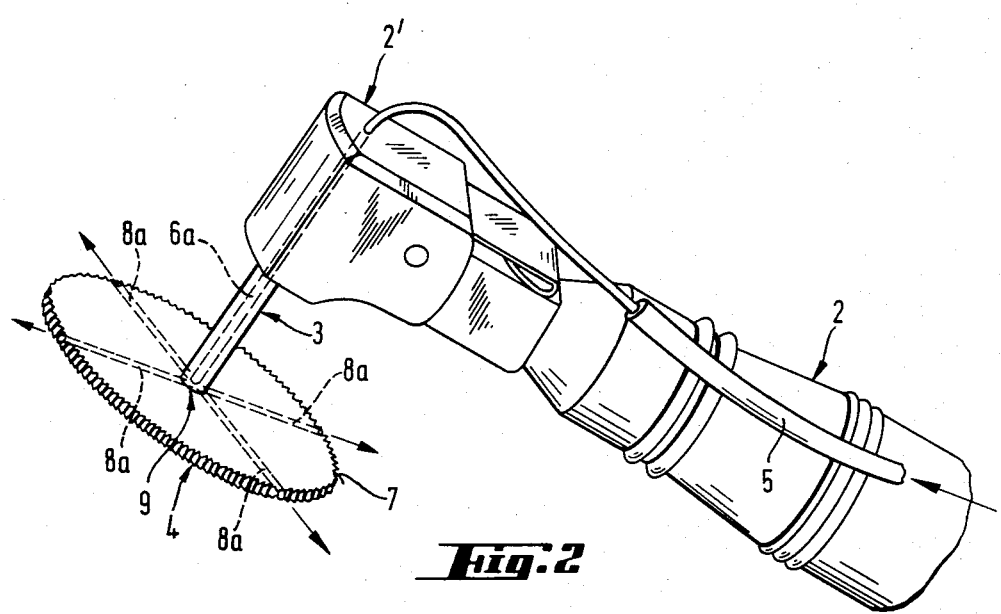
Figure 3:
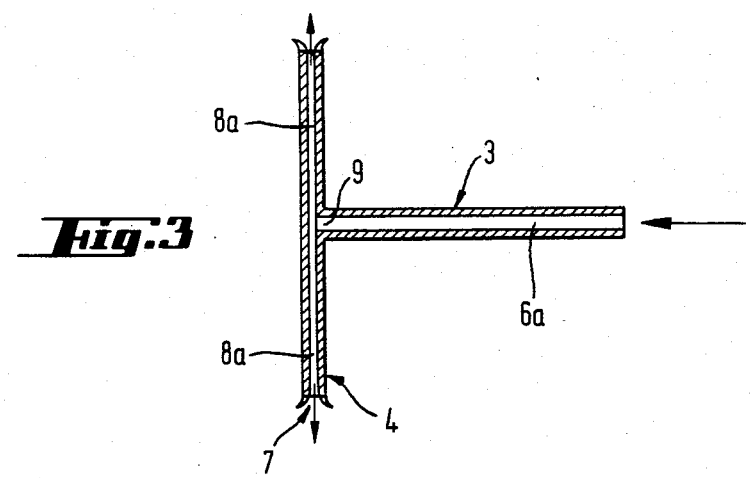
Figure 4:
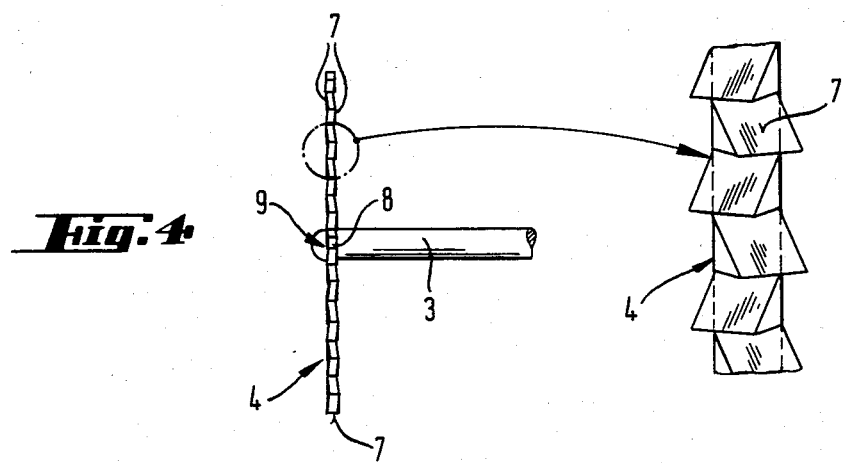
Figure 5:
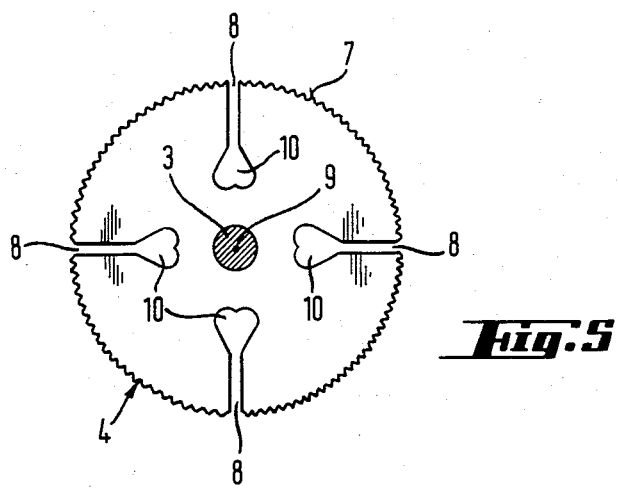

In the drawing,

FIG. 1 is a perspective view showing a handpiece and an anglepiece, a circular saw, which has been inserted into the anglepiece, and means for supplying and guiding coolant, FIG. 2 is a view which is similar to FIG. 1 and shows different means for supplying a coolant, FIG. 3 is a transverse sectional view showing the saw of FIG. 2, FIG. 4 is a side elevation showing the saws of FIGS. 1 and 2, FIG. 5 is a top plan view showing the sawblade of FIG. 1 and FIG. 6 represents the cross-section of a slot.

The drawing shows a handpiece 2 and a anglepiece 2', which is attached to the handpiece 2. The shaft 3 carrying the sawblade 4 is gripped in the chuck of the anglepiece 2'. Coolant is supplied through the hose 5.

The center 9 of the sawblade 4 is surrounded by a circular series of apertures 10. The outlet end 6 of the coolant hose 5 is disposed over the circular series of apertures 10. The coolant discharged from the hose 5 enters the apertures 10 and under centrifugal force is thrown through the slots 8 to the periphery 7 of the sawblade 4, which is provided at its periphery with set teeth, each of the teeth being set in a lateral direction opposite to the lateral direction of adjacent teeth, which tend to retain the coolant so that the latter will finally flow to the cutting region disposed at a large depth.

In accordance with FIGS. 2 and 3 the coolant is supplied and guided via the bore 6a of the drive shaft 3 to the radial bores 8a in the sawblade 4, which has a larger thickness.

FIG. 6 shows a jaw 11, which has been formed with a wedge-shaped slot 12 by means of three sawblades 4a, 4b, 4c, which increase in thickness in that order. The corrugated implant 13 is then inserted into the downwardly tapering slot 12.

What is claimed is:

1. In a dental rotary instrument, which is adapted to be driven by a dental handpiece and to cut a slot for receiving an implant into a jaw,
   the improvement which comprises
   a rotary sawblade, which has a circular periphery and is provided at said periphery with sawteeth and is formed with a plurality of angularly spaced apart, radial passages, which open at said periphery,
   driving means, connected to a dental handpiece to transmit torque from said handpiece to said sawblade for rotating the latter, and
   coolant supply and guiding means disposed within said sawblade and connected to said dental handpiece to supply and guide a coolant from said handpiece to each of said radial passages at a point which is radially inwardly spaced from said periphery, said sawteeth being set at said periphery so as to retain the coolant flow at the cutting region of said sawblade.

2. The improvement set forth in claim 1, wherein said radial passages consist of radial grooves.

3. The improvement set forth in claim 1, wherein said radial passages consist of radial slots.

4. The improvement set forth in claim 1, wherein said radial passaages consist of diametrical bores.

5. The improvement as set forth in claim 4, wherein said driving and coolant supply and guiding means comprise a shaft, which is non-rotatably connected to said sawblade and is adapted to be connected to said sawblade and is adapted to be connected to said handpiece and to transmit torque from said handpiece to said sawblade, and said shaft is formed with an axial bore, which communicates with said diametrical bores and is adapted to supply coolant from said handpiece to said diametrical bores, via the center of said sawblade.

6. The improvement set forth in claim 1, wherein said sawblade is formed with a plurality of apertures, which are arranged in a circular series and disposed at the radially inner ends of respective ones of said radial passages, each of said radial passages is open only on one side of said sawblade, and said driving and coolant supply and guiding means are adapted to supply said coolant to each of said apertures.

7. The improvement set forth in claim 6, wherein said driving and coolant supply and guiding means comprise a hose, which is adapted to be connected to said handpiece and has an open end disposed over said circular series of apertures on the side of the sawblade which faces said handpiece when said driving and coolant supply means are connected to said handpiece.

8. The improvement set forth in claim 6, wherein each of said apertures has a cardioid configuration and has a radially outwardly directed apex and said radial passages extend from said apices.

9. In a dental rotary cutting instrument, which is adapted to be driven by a dental handpiece, and to cut a slot for receiving an implant into a jaw, the improvement which comprises a sawblade, which has a circular periphery and is provided at said periphery with sawteeth which are set so as to retain coolant flow at the cutting region of said sawblade, and is formed with a plurality of angularly spaced apart, radial passages, which open at said periphery, said sawblade is adapted to be connected to said handpiece and to be rotated by said handpiece, and to receive coolant from said handpiece in said passages at points which are spaced radially inwardly from said periphery.

10. The improvement set forth in claim 9, wherein said sawblade is formed with a plurality of apertures, which are arranged in a circular series and disposed at the radially inner ends of respective ones of said radial passages, each of said radial passages is open only on one side of said sawblade, and said apertures are adapted to receive said coolant from said handpiece.

11. The improvement set forth in claim 10, wherein each of said apertures has a cardioid configuration and has a radially outwardly directed apex and said radial passages extend from said apices.

12. In a method of cutting a slot for receiving an implant into a bore by means of a dental rotary cutting instrument, which is adapted to be driven by a dental handpiece, the improvement residing in using an instrument which comprises sawblades, which have a circular periphery and are provided at said periphery with sawteeth, and are formed with a plurality of angularly spaced apart, radial passages, which open at said periphery, said sawteeth being set to retain the coolant flow at the cutting region of said sawblades, driving and coolant supply and guiding means, which are adapted to be connected to a dental handpiece and to transmit torque from said handpiece to said sawblades to rotate the latter, and are adapted to supply and guide a coolant from said handpiece to each of said radial passages at a point which is radially inwardly spaced from said periphery, said coolant supply and guiding means being formed within said sawblades, and using progressively thinner ones of said sawblades in successive steps to cut said slot to progressively larger depths, so as to form a downwardly tapering slot.

* * * * *